United States Patent [19]

Holmwood et al.

[11] Patent Number: 4,525,204
[45] Date of Patent: Jun. 25, 1985

[54] METHOD AND COMPOSITIONS FOR REGULATING PLANT GROWTH USING PYRIMIDINE-BUTANOL COMPOUNDS

[75] Inventors: Graham Holmwood, Wuppertal; Klaus Lürssen, Bergisch-Gladbach, both of Fed. Rep. of Germany

[73] Assignee: Bayer Aktiengesellschaft, Leverkusen, Fed. Rep. of Germany

[21] Appl. No.: 200,170

[22] Filed: Oct. 24, 1980

[30] Foreign Application Priority Data

Nov. 7, 1979 [DE] Fed. Rep. of Germany ....... 2944850

[51] Int. Cl.³ ...................... A01N 9/22; C07D 239/26
[52] U.S. Cl. ........................................ 71/92; 544/334; 544/335; 71/76; 71/78
[58] Field of Search ................ 71/92, 78, 76; 544/335

[56] References Cited

U.S. PATENT DOCUMENTS 3,818,009  6/1974  Taylor et al. ............................. 71/92
3,869,456  3/1975  Taylor et al. ........................ 424/251
4,007,200  2/1977  Panzer et al. ........................ 544/335

FOREIGN PATENT DOCUMENTS 0001399  4/1979  European Pat. Off. .
2742173  3/1979  Fed. Rep. of Germany .

Primary Examiner—Glennon H. Hollrah
Assistant Examiner—James H. Turnipseed
Attorney, Agent, or Firm—Felfe & Lynch

[57] ABSTRACT

Pyrimidine-butanol derivatives of the general formula

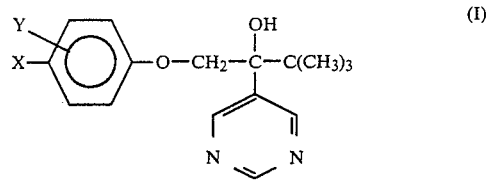

in which
X represents hydrogen, halogen, alkyl or alkoxy, or represents benzyloxy which is optionally substituted by halogen and
Y represents hydrogen or halogen have powerful growth-regulating properties.

8 Claims, No Drawings

METHOD AND COMPOSITIONS FOR REGULATING PLANT GROWTH USING PYRIMIDINE-BUTANOL COMPOUNDS

The present invention relates to plant growth regulating compositions, and to methods for regulating plant growth, using certain pyrimidine-butanol derivatives.

It is known that certain pyrimidine-butanol derivatives have fungicidal properties, from DE-OS (German Published Specification) No. 2,742,173.

It is also known that certain pyrimidine derivatives, for example alpha-(2-chlorophenyl)-alpha-(4-fluorophenyl)-5-pyrimidinemethanol, inter alia, also display growth-regulating properties (see U.S. Pat. No. 3,818,009 and 3,869,456). However, the activity of these substances is not always completely satisfactory, especially when small amounts are applied.

It has now been found that the pyrimidine-butanol derivatives of the general formula

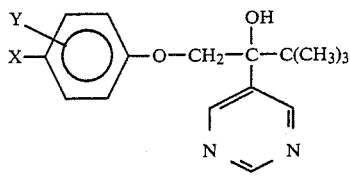

in which
X represents hydrogen, halogen, alkyl or alkoxy, or represents benzyloxy which is optionally substituted by halogen and
Y represents hydrogen or halogen have powerful growth-regulating properties.

Accordingly, the present invention provides a method of regulating the growth of plants in which there is applied to the plants, or to a habitat thereof, a compound of the formula (I), alone or in admixture with a diluent or carrier.

The compounds of formula (I) possess an asymmetric carbon atom; they can thus exist in the form of the two optical isomers or as a racemate.

Surprisingly, the pyrimidine-butanol derivatives of the formula (I) which can be used according to the invention exhibit a better plant growth-regulating action than the known pyrimidine derivatives α-(4-fluorophenyl)-α-phenyl-5-pyrimidinemethanol and α-(2-chlorophenyl)-α-(4-fluorophenyl)-5-pyrimidinemethanol, which are closely related compounds chemically and from the point of view of their action. The use, according to the invention, of the pyrimidine-butanol derivatives thus represents an enrichment of the art.

The formula (I) provides a general definition of the pyrimidine-butanol derivatives which can be used according to the invention. Preferably, in this formula, X represents hydrogen, fluorine, chlorine, bromine, alkyl with 1 to 4 carbon atoms, alkoxy with 1 to 4 carbon atoms or benzyloxy which is optionally substituted by chlorine, and
Y represents hydrogen, fluorine, chlorine or bromine.

Very particularly preferred compounds of the formula (I) are those in which X represents hydrogen, fluorine, chlorine, methyl, ethyl, isopropyl, methoxy, ethoxy, isopropoxy, benzyloxy or chlorobenzyloxy, and Y represents hydrogen, chlorine or fluorine.

The pyrimidine-butanol derivatives which can be used according to the invention are known (see DE-OS (German Published Specification) 2,742,173). They can be prepared by reacting phenoxymethyl tert.-butyl ketones of the general formula

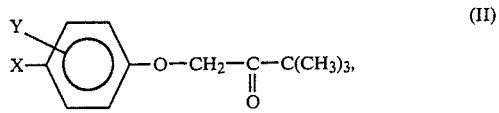

in which
X and Y have the meanings indicated above, with a 5-halogeno-pyrimidine of the general formula

in which
Hal represents hydrogen,
in the presence of an inert organic solvent or solvent mixture, for example diethyl ether or tetrahydrofuran, and in the presence of an alkali metal-organic compound, for example n-butyl-lithium, as a base, at temperatures between $-150°$ C. and $-50°$ C. and under an inert gas, for example nitrogen. To isolate the end products, the reaction mixture is worked up in the customary manner and the end products are purified; if appropriate, an acid addition salt or a metal salt complex is prepared.

The active compounds which can be used according to the invention engage in the metabolism of the plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants on their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds, at verges, at airports or in fruit orchards. The inhibition of growth of herbaceous and woody plants at verges and in the vicinity of pipelines or overland lines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging.

Use of growth regulators for shortening and strengthening the stem enables higher amounts of fertiliser to be applied to increase the yield, without danger of the cereal lodging.

In the case of many crop plants, inhibition of the vegetative growth permits denser planting of the crop, so that a greater yield per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants and also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example, in the case of tobacco, tomatoes or coffee.

Using growth regulators it is also possible to influence the latent period of seeds or buds of plants, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Finally, the resistance of plants to frost, drought or a high salt content in the soil can be induced with growth regulators. Cultivation of plants in regions which are usually unsuitable for this purpose thereby becomes possible.

It should be particularly emphasised that the compounds according to the invention also inhibit growth in rice.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds can be converted into the customary formulations, such as solutions, emulsions, suspensions, powders, foams, pastes, granules, aerosols, very fine capsules in polymeric substances and in coating compositions, for use on seed, as well as ULV formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides and herbicides, and also as a mixture with fertilisers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomising, scattering, dusting, foaming and coating. Furthermore it is possible to apply the active compounds in accordance with the ultra-low-volume method, to spread the active compound preparation or the active compound itself on plants or parts of plants or to inject the active compound preparation or the active compound itself into the soil. It is also possible to treat the seeds of plants.

The amounts applied can be varied within a substantial range. In general, 0.01 to 50 kg, preferably 0.05 to 10 kg, of the active compound are employed per hectare of soil surface.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The plant-growth-regulating activity of the compounds of this invention is illustrated by the following biotest Examples.

In these Examples, the compounds according to the present invention are each identified by the number (given in brackets) of the corresponding preparative Example, which will be found later in this specification.

The known comparison compounds are identified as follows:

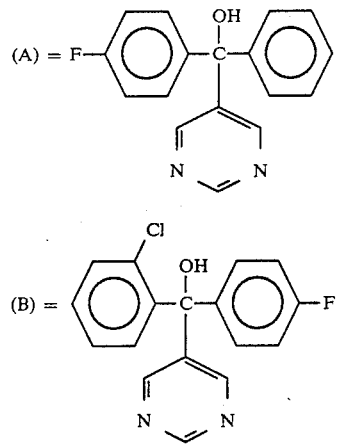

EXAMPLE A

Inhibition of Growth of Side Shoots of Tobacco

Solvent: 30 parts by weight of dimethylformamide.
Emulsifier: 1 part by weight of polyoxyethylene sorbitan monolaurate.

To produce a suitable preparation of active compound, 1 part by weight of active compound was mixed with the stated amounts of solvent and emulsifier and the mixture was made up to the desired concentration with water.

Tobacco plants were grown in a greenhouse until the 7th secondary leaf had unfolded. In this stage, the apical vegetative tips were removed and the plants were sprayed with the preparations of active compound until dripping wet. After 3 weeks, the side shoots of the plants were broken off and weighed. The weight of the side shoots of the treated plants was compared with that of the control plants. 100% inhibition denoted the absence of side shoots and 0% denoted a growth of side shoots which corresponded to that of the control plants.

The active compounds, active compound concentrations and results can be seen from the following table.

TABLE A

| Active Compound | Inhibition of growth of side shoots of tobacco | |
|---|---|---|
| | Concentration in % | Inhibition of growth in % |
| (1) | 0.2 | 76 |
| (control) | — | 0 |

EXAMPLE B

Inhibition of Growth of Soya Beans

Solvent: 30 parts by weight of dimethylformamide.
Emulsifier: 1 part by weight of polyoxyethylene sorbitan monolaurate.

To produce a suitable preparation of active compound, 1 part by weight of active compound was mixed with the stated amounts of solvent and emulsifier and the mixture was made up to the desired concentration with water.

Soya bean plants were grown in a greenhouse until the first secondary leaf had unfolded completely. In this stage, the plants were sprayed with the preparations of active compound until dripping wet. After 3 weeks, the additional growth was measured on all the plants and the inhibition of growth in percent of the additional growth of the control plants was calculated. 100% inhibition of growth meant that growth had stopped and 0% denoted a growth corresponding to that of the control plants.

The active compounds, active compound concentrations and results can be seen from the following table.

TABLE B

| Inhibition of growth of soya beans | | |
|---|---|---|
| Active compound | Concentration in % | Inhibition of growth in % |
| (1) | 0.05 | 100 |
| (2) | 0.05 | 80* |
| (3) | 0.05 | 50 |
| (5) | 0.05 | 85* |
| (7) | 0.05 | 70* ** |
| (8) | 0.05 | 30* |
| — | — | 0 |
| (control) | | |

*increased formation of side shoots
**dark green leaf coloration

EXAMPLE C

Inhibition of Growth of Woody Plants (Acer)

Solvent: 30 parts by weight of dimethylformamide.
Emulsifier: 1 part by weight of polyoxyethylene sorbitan monolaurate.

To produce a suitable preparation of active compound, 1 part by weight of active compound was mixed with the stated amounts of solvent and emulsifier and the mixture was made up to the desired concentration with water.

One year old seedlings which had grown to a height of 25 cm were sprayed with the preparations of active compound until dripping wet. After 6 weeks' growth in a greenhouse, the additional growth was measured and the inhibition of growth was calculated in percent of the additional growth of the control plants. 100% inhibition of growth meant that growth had stopped and 0% meant a growth corresponding to that of the control plants.

The active compounds, active compound concentrations and results can be seen from the following table.

TABLE C

| Inhibition of growth of woody plants (Acer) | | |
|---|---|---|
| Active compound | Concentration in % | Inhibition of growth in % |
| (1) | 0.2 | 91 |
| — | — | 0 |
| (control) | | |

EXAMPLE D

Inhibition of Growth of Woody Plants (Alnus)

Solvent: 30 parts by weight of dimethylformamide.
Emulsifier: 1 part by weight of polyoxyethylene sorbitan monolaurate.

To produce a suitable preparation of active compound, 1 part by weight of active compound was mixed with the stated amounts of solvent and emulsifier and the mixture was made up to the desired concentration with water.

One year old seedlings which had grown to a height of 25 cm were sprayed with the preparations of active compound until dripping wet. After 6 weeks' growth in a greenhouse, the additional growth was measured and the inhibition of growth was calculated in percent of the additional growth of the control plants. 100% inhibition of growth meant that growth had stopped and 0% meant a growth corresponding to that of the control plants.

The active compounds, active compound concentrations and results can be seen from the following table.

TABLE D

| Inhibition of growth of woody plants (Alnus) | | |
|---|---|---|
| Active compound | Concentration in % | Inhibition of growth in % |
| (1) | 0.2 | 77 |
|  | 0.4 | 84 |
| — | — | 0 |
| (control) | | |

EXAMPLE E

Inhibition of Growth of Grass (*Festuca pratensis*)

Solvent: 30 parts by weight of dimethylformamide.
Emulsifier: 1 part by weight of polyoxyethylene sorbitan monolaurate.

To produce a suitable preparation of active compound, 1 part by weight of active compound was mixed with the stated amounts of solvent and emulsifier and the mixture was made up to the desired concentration with water.

Grass (*Festuca pratensis*) was grown in a greenhouse up to a height in growth of 5 cm. In this stage, the plants are sprayed with the preparations of active compound until dripping wet. After 3 weeks, the additional growth was measured and the inhibition of growth in percent of the additional growth of the control plants was calculated. 100% inhibition of growth meant that growth had stopped and 0% denoted a growth corresponding to that of the control plants.

The active compounds, active compound concentrations and results can be seen from the following table.

TABLE E

| Inhibition of growth of grass (*Festuca pratensis*) | | |
|---|---|---|
| Active compound | Concentration in % | Inhibition of growth in % |
| (1) | 0.05 | 90 |
| (4) | 0.05 | 70 |
| (7) | 0.05 | 55 |
| — | — | 0 |
| (control) | | |
| (A) (known) | 0.05 | 0 |
| (B) (known) | 0.05 | 0 |

EXAMPLE F

Inhibition of Growth of Barley

Solvent: 30 parts by weight of dimethylformamide.
Emulsifier: 1 part by weight of polyoxyethylene sorbitan monolaurate.

To produce a suitable preparation of active compound, 1 part by weight of active compound was mixed with the stated amounts of solvent and emulsifier and the mixture was made up to the desired concentration with water.

Barley plants were grown in a greenhouse to the 2-leaf stage. In this stage, the plants were sprayed with the preparations of active compound until dripping wet. After 3 weeks, the additional growth was measured on all plants and the inhibition of growth in percent of the additional growth of the control plants was calculated. 100% inhibition of growth meant that growth had stopped and 0% denoted a growth corresponding to that of the control plants.

The active compounds, active compound concentrations and results can be seen from the following table.

TABLE F

| Active compound | Inhibition of growth of barley | |
|---|---|---|
| | Concentration in % | Inhibition of growth in % |
| (1) | 0.050 | 42 |
| | 0.025 | 24 |
| (4) | 0.050 | 35 |
| (5) | 0.050 | 25 |
| (6) | 0.050 | 50 |
| (8) | 0.050 | 75 |
| — | — | 0 |
| (control) | | |
| (A) (known) | 0.05 | 0 |
| (B) (known) | 0.05 | 0 |

EXAMPLE G

Influence on Growth of Sugar Beet

Solvent: 30 parts by weight of dimethylformamide.
Emulsifier: 1 part by weight of polyoxyethylene sorbitan monolaurate.

To produce a suitable preparation of active compound, 1 part by weight of active compound was mixed with the stated amounts of solvent and emulsifier and the mixture was made up to the desired concentration with water.

Sugar beet was grown in a greenhouse until formation of the cotyledons was complete. In this stage, the plants were sprayed with the preparations of active compound until dripping wet. After 14 days, the additional growth of the plants was measured and the influence on growth in percent of the additional growth of the control plants was calculated. 0% influence on growth denoted a growth which corresponded to that of the control plants. Negative values characterised an inhibition of growth in comparison to the control plants, whilst positive values characterised a promotion of growth in comparison to the control plants.

The active compounds, active compound concentrations and results can be seen from the following Table.

TABLE G

| Active compound | Influence on growth of sugar beet | |
|---|---|---|
| | Concentration in % | Inhibition of growth in % |
| (1) | 0.05 | −90* ** |
| (2) | 0.05 | −65* ** |
| (8) | 0.05 | −30* ** |
| (3) | 0.05 | −75 |
| (4) | 0.05 | −75* ** |
| (5) | 0.05 | −80* ** |
| (6) | 0.05 | −75* ** |
| (7) | 0.05 | −75 |

TABLE G-continued

| Active compound | Influence on growth of sugar beet | |
|---|---|---|
| | Concentration in % | Inhibition of growth in % |
| (A) (known) | 0.05 | −10* ** |
| (B) (known) | 0.05 | −30* ** |
| (control) | — | =0 |

*dark green leaves
**particularly thick leaves

EXAMPLE H

Inhibition of Growth of Rice

Solvent: 30 parts by weight of dimethylformamide.
Emulsifier: 1 part by weight of polyoxyethylene sorbitan monolaurate.

To produce a suitable preparation of active compound, 1 part by weight of active compound was mixed with the stated amounts of solvent and emulsifier and the mixture was made up to the desired concentration with water.

Rice plants were grown to the 2-leaf stage in soil in 10×10×10 cm pots in a greenhouse. In this stage, the plants were sprayed with the preparations of active compound until dripping wet. After 10 days, the additional growth was measured on all plants and the inhibition of growth in percent of the additional growth of the control plants was calculated. 100% inhibition of growth meant that growth had stopped and 0% denoted a growth corresponding to that of the control plants.

Further experimental data and the results of this experiment can be seen from the following table.

TABLE H

| Active compound | Inhibition of growth of rice | |
|---|---|---|
| | Concentration in % | Inhibition of growth in % |
| (7) | 0.0125 | 9 |
| | 0.0250 | 35 |
| | 0.0500 | 57 |
| (4) | 0.0125 | 26 |
| (3) | 0.0125 | 10 |
| (1) | 0.0125 | 4 |
| | 0.0250 | 17 |
| (2) | 0.0125 | 17 |
| (5) | 0.0125 | 17 |
| control | — | =0 |

EXAMPLE I

Inhibition of Growth of Paddy Rice var. Nihonbare 5 parts of active compound were mixed with 2.5 parts of Newkalgen CP-50, 30 parts of bentonite and 62.5 parts of talc in a mixer. 20 parts of water were added. The sludge was pressed through holes 0.5 mm in diameter and dried. Granules with a particle size of 0.5 mm diameter and about 0.7 mm length resulted.

Plants which were 10 days old were planted into dishes 25×20×10 cm in size, in which the soil was covered by water. After 10 days, the preparation of active compound was introduced into the water. After a further 14 days, the height to which the plants had grown was measured.

In this test, the compounds (2), (4), (5), (7) and (3) exhibited a very good growth-inhibiting activity.

PREPARATIVE EXAMPLES

EXAMPLE 1

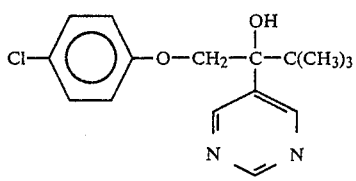 (I)

A solution of 22.65 g (0.1 mol) of 1-(4-chlorophenoxy)-3,3-dimethyl-butan-2-one in 110 ml of absolute tetrahydrofuran and 70 ml of absolute ether was cooled to −120° C. under a dry nitrogen atmosphere. A solution of 15.9 g (0.1 mol) of 5-bromopyrimidine in 50 ml of absolute tetrahydrofuran was added dropwise to this solution. 50 ml of a 15% strength solution of n-butyl-lithium in n-hexane were then slowly added dropwise at −120° C. The mixture was subsequently stirred, first at a temperature of about −110° C. for 2 hours and then at −78° C. overnight. The reaction mixture was warmed to room temperature, 100 ml of 10% strength ammonium chloride solution and 200 ml of ethyl acetate were added and the aqueous phase was separated off. The organic phase was washed once with 1 N hydrochloric acid and then twice with saturated sodium chloride solution, dried over sodium sulphate and concentrated. The residue was suspended in ether and the solid was filtered off and recrystallised from acetonitrile. 12.3 g (50% of theory, relative to n-butyl-lithium) of 1-(4-chlorophenoxy)-3,3-dimethyl-2-(pyrimidin-5-yl)-butan-2-ol of melting point 172°–174° C. were obtained.

The compounds of the general formula

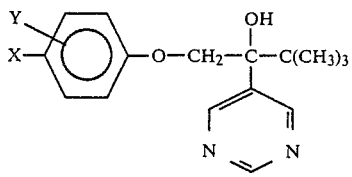 (I)

listed in the following table 1 were obtained analogously:

TABLE 1

| Example No. | X | Y | Melting Point (°C.) |
|---|---|---|---|
| 2 | H | H | 127–29 |

TABLE 1-continued

| Example No. | X | Y | Melting Point (°C.) |
|---|---|---|---|
| 3 | CH$_3$O— | H | 136–37 |
| 4 | F | H | 163.5–64.5 |
| 5 | Cl | 2-Cl | 96–99 |
| 6 | Cl | 3-Cl | 155–57 |
| 7 | CH$_3$ | H | 152–53.5 |
| 8 | 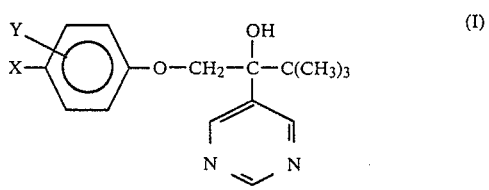 | H | 122–24 |

It will be understood that the specification and examples are illustrative but not limitative of the present invention and that other embodiments within the spirit and scope of the invention will suggest themselves to those skilled in the art.

What is claimed is:

1. Method for regulating the growth of plants which method comprises applying to the plants and their habitat, an effective amount of a pyrimidine-butanol compound of the formula:

(I)

wherein
X is hydrogen, fluorine, chlorine, methyl, methoxy, and benzyloxy; and
Y is hydrogen or chlorine.

2. Method as claimed in claim 1 wherein said compound is 1-(4-chlorophenoxy)-3,3-dimethyl-2-(pyrimidine-5-yl)-butan-2-ol.

3. Method as claimed in claim 1 wherein said compound is 1-phenoxy-3,3-dimethyl-2-(pyrimidine-5-yl)-butan-2-ol.

4. Method as claimed in claim 1 wherein said compound is 1-(4-fluorophenoxy)-3,3-dimethyl-2-(pyrimidine-5-yl)-butan-2-ol.

5. Method as claimed in claim 1 wherein said compound is 1-(4-methylphenoxy)-3,3-dimethyl-2-(pyrimidine-5-yl)-butan-2-ol.

6. Method as claimed in claim 1 wherein 0.01 to 50 kg of the active compound is applied per hectare.

7. Method as claimed in claim 1 wherein 0.05 to 10 kg of the active compound are applied per hectare.

8. Method as claimed in claim 1 wherein the plants are rice plants.

* * * * *